United States Patent [19]

Lin et al.

[11] 4,429,046
[45] Jan. 31, 1984

[54] LARGE SCALE CULTIVATION OF BORDETELLA PERTUSSIS CELLS FOR VACCINE PRODUCTION

[75] Inventors: Wenlii Lin, New City, N.Y.; John W. Imbaratto, Hamburg, N.J.

[73] Assignee: American Cyanamid Company, Stamford, Conn.

[21] Appl. No.: 401,999

[22] Filed: Jul. 26, 1982

[51] Int. Cl.³ .................... C12N 1/20; A61K 39/02
[52] U.S. Cl. ................................. 435/253; 424/92
[58] Field of Search ................................. 435/253

[56] References Cited

U.S. PATENT DOCUMENTS 3,577,319  5/1971  Nielsen et al. ............... 435/253

Primary Examiner—Lionel M. Shapiro
Attorney, Agent, or Firm—Robert P. Raymond

[57] ABSTRACT

A *Bordetella pertussis* vaccine is prepared by deep tank cultivation using a seed grown in a biphasic culture system. An anion exchange resin and a Modified Cohen-Wheeler medium used in the process, results in increased antigenicity and a minimization of toxicity in the phase I *Bordetella pertussis* vaccine.

7 Claims, No Drawings

LARGE SCALE CULTIVATION OF *BORDETELLA PERTUSSIS* CELLS FOR VACCINE PRODUCTION

SUMMARY OF THE INVENTION

The present invention relates to an improvement in the process of deep tank cultivation of *Bordetella pertussis* of U.S. Pat. No. 3,577,319, the teaching of which is incorporated by reference. More particularly, it concerns a process involving a combination of biphasic and liquid growth. The initial subcultures are conducted on biphasic blood agar which replaces the blood agar slant. The organisms from this biphasic blood agar growth are transferred to a secondary biphasic culture consisting of Cohen-Wheeler liquid medium. After suitable growth, the liquid portion is used to inoculate Modified Cohen-Wheeler liquid medium containing an anion exchange resin such as DOWEX® 1-X8 or the like, in a larger vessel, for example, 5 gallons. After suitable growth, this liquid culture is used to inoculate Modified Cohen-Wheeler liquid medium containing anion exchange resin as hereinabove described in a larger, deep tank, for example, 125 gallons. After suitable growth in the tank, the organisms are killed, separated from the broth, and then suspended in buffered saline to produce the final vaccine. The last step in the tank is the same as the process formerly used.

Also as in the former process, the operations are carried out aseptically, as far as contamination with other organisms is concerned, but because of the biphasic culturing and the incorporation of purity checks, there is minimum loss of production.

DESCRIPTION OF THE PREFERRED EMBODIMENT

The incubated biphasic agars are inoculated at about 35° C. Microscopic examination and purity checks follow all subculturing. The blood agar flasks contain 100 ml of Bordet-Gengou Agar-plus 15-25% sheep or rabbit blood overlaid with 25 ml of Cohen-Wheeler Medium Modified having the following composition:

|  | Parts |
| --- | --- |
| Casamino Acids | 10 |
| Sodium Chloride | 2.5 |
| Monopotassium Phosphate | 0.5 |
| Magnesium Chloride | 0.1 |
| Soluble Starch | 1.5 |
| Calcium Chloride | 0.01 |
| Ferrous Sulphate | 0.01 |
| Copper Sulphate | 0.005 |
| Glutathione | 0.025 |
| Yeast Extract Dialyzate | 75 |
| Distilled Water | 1,000 |

The flasks are inoculated with 1-2 ml of cell suspension stock stored in liquid nitrogen, inoculated at 35° C. and continuously shaken at 60-80 strokes per minute. The incubation lasts for 20-30 hours. Storage of the *Bordetella pertussis* seed cells at liquid nitrogen temperatures are important to the results obtained.

The broth from the blood agar culture (2-5%) is transferred to a 5 liter toxin bottle containing 500 ml of Cohen-Wheeler charcoal agar overlaid with 200 ml of Cohen-Wheeler Medium Modified, incubated at 35° C. and continuously shaken at 60-80 strokes per minute. The incubation lasts for 20-30 hours.

The broth from the charcoal culture (2-5%) is transferred to a bottle containing 3 liters of Cohen-Wheeler Medium Modified with 3 g of Dowex® 1-X8 resin or the like, and incubated at 35° C., continuously shaken for 60-80 strokes per minute. The incubation lasts for 20-30 hours. This culture is used to inoculate the fermentation tank.

Another important aspect of the deep tank culture procedure of the present invention concerns the addition of an anion exchange resin to the fermentation composition. Basic anion exchange resins are preferred for use therein. Dowex 1-X8 is most preferred as the anion exchange resin.

The fermentation tank containing approximately 300 liters of distilled water is sanitized for a minimum of one hour at 120°-123° C. Once cooled, it is drained, charged with 400 g of Dowex 1-X8 resin or the like, and 400 liters of the Cohen-Wheeler Medium Modified is pumped into the tank and sterilized for 35 minutes at 120°-123° C. The tank is cooled to 32°-38° C. and held overnight under 10 lbs sterile air pressure.

The culture from the liquid medium is inoculated into the fermentation tank and allowed to grow for 20-30 hours at 32°-38° C. with agitation and with the addition of 3 cubic feet of surface aeration.

After completion of fermentation, the tank is inactivated with a solution of sodium ethylmercurithiosalicylate to a final concentration of 0.01-0.2%. The contents of the vessel is cooled to about 20° C. and centrifuged at 15,000 rpm. The packed bacterial cells are collected by scraping the bowl of the centrifuge and suspended in phosphate buffered saline, 0.85% solution containing 0.01% sodium ethylmercurithiosalicylate. The suspension is detoxified at 20°-25° C. for 2-10 days. The stock is stored at 4° C.

The vaccines produced since implementing the hereinabove described modifications to U.S. Pat. No. 3,577,319 have resulted in a dramatic reduction in production batch failures previously due to toxicity or low potency. See Table I.

TABLE I

| Medium | Number of Batches | % Sucess |
| --- | --- | --- |
| Conventional Liquid Medium Without Resin | 109 | 53% |
| Liquid Medium With DOWEX 1-X8 Resin and Modified Cohen-Wheeler Medium | 18 | 100% |

The process of the present invention results in enhanced bacterial growth and enriched antigenicity of the vaccine with consequent minimization of the tendency to produce side effects upon injection into the human body.

We claim:

1. A process for producing Pertussis Vaccine of high potency and low toxicity which comprises:
   (a) producing seed cultures of *Bordetella pertussis* from a biphasic growth in blood agar;
   (b) inoculating a biphasic growth system comprising a liquid medium over charcoal agar with said seed system;
   (c) inoculating said charcoal biphasic seed into a liquid medium containing an anion exchange resin;
   (d) inoculating a deep fermentation tank with liquid medium culture containing an anion exchange resin;

(e) incubating the broth at a temperature of 32°–38° C.;

(f) killing the *Bordetella pertussis* and separating the killed bacteria from the broth.

2. A process according to claim 1 in which the resin in the liquid medium is a basic anion exchange resin.

3. A process according to claim 1 in which the labeled and separated *Bordetella pertussis* bacteria are suspended in isotonic saline.

4. A process according to claim 2 in which the killed and separated *Bordetella pertussis* bacteria are suspended in isotonic saline.

5. A process according to claim 1 in which the separated killed *Bordetella pertussis* bacteria are asceptically dispersed and suspended in saline.

6. A process according to claim 2 in which the separated killed *Bordetella pertussis* bacteria are asceptically dispersed and suspended in saline.

7. A process of claim 1 wherein the seed cultures are stored at liquid nitrogen temperatures.

* * * * *